(12) United States Patent
Stephens

(10) Patent No.: US 7,045,098 B2
(45) Date of Patent: May 16, 2006

(54) APPARATUS AND METHOD FOR REMOVING INTERFERING SUBSTANCES FROM A URINE SAMPLE USING A CHEMICAL OXIDANT

(76) Inventor: James Matthew Stephens, P.O. Box 8189, Cincinnati, OH (US) 45208

( * ) Notice: Subject to any disclaimer, the term of this patent is extended or adjusted under 35 U.S.C. 154(b) by 0 days.

(21) Appl. No.: 09/776,222

(22) Filed: Feb. 2, 2001

(65) Prior Publication Data

US 2002/0061563 A1 May 23, 2002

(51) Int. Cl.
*A61M 1/00* (2006.01)
*B01L 3/00* (2006.01)

(52) U.S. Cl. .................. 422/102; 422/99; 422/101; 604/327; 604/317; 206/438; 210/348; 210/464

(58) Field of Classification Search ............... 604/327, 604/317; 206/438; 422/99, 102, 101; 210/348, 210/464
See application file for complete search history.

(56) References Cited

U.S. PATENT DOCUMENTS

| | | | |
|---|---|---|---|
| 3,771,964 A | 11/1973 | Fader | 23/253 TP |
| 3,966,764 A | 6/1976 | Goldstein et al. | 260/326.85 |
| 4,038,031 A | 7/1977 | Lam | 23/230 B |
| 4,242,446 A | 12/1980 | Madappally et al. | 435/15 |
| 4,270,923 A | 6/1981 | Kondo et al. | 23/230 B |
| 4,536,478 A | 8/1985 | Sokoloff et al. | 436/533 |
| 4,606,736 A * | 8/1986 | Van De Weghe | 604/322 |

(Continued)

FOREIGN PATENT DOCUMENTS

WO  WO 90/12113 A1  10/1990

OTHER PUBLICATIONS

S. Kaye, "A rapid screening blood alcohol analysis for the local pathologist", *American Jr. Forensic Medicine and Pathology*, vol. 1, No. 3, pp. 205–208, Sep. 1980.

S. Mikkelsen et al., "Adulterants Causing False Negatives in Illicit Drug Testing", *Clin. Chem.*, vol. 343, No. 11, pp. 2333–2336, 1988 (no month).

A. Warner, "Interference of Common Household Chemical in Immunoassay Methods for Drugs of Abuse", *Clin. Chem.*, vol. 35, No. 4, pp. 648–651, 1989 (no month).

J. Cody et al. "Impact of Adulterants on RIA Analysis of Urine for Drugs of Abuse", *Jr. Anal. Toxicol.*, vol. 13, pp. 277–284, 1989 (no month).

P. Nebinger et al., "Interference in Immunological Urine Tests for Drugs of Abuse by Adulterants", *LRA*, vol. 3, pp. 237–239, 1991 (no month).

R. Schwarzhoff, "The Effects of Adulterating Agents on FPIA Analysis of Urine for Drugs of Abuse", *Jr. Anal. Toxicology*, vol. 17, pp. 14–17, Feb. 1993.

D. Armbruster et al., "Cloned Enzyme Donor Immunoassay (CEDIA) for Drugs–of–Abuse Screening", *Clin. Chem.*, vol. 41, No. 1, pp. 92–98, 1995.

(Continued)

*Primary Examiner*—Jill Warden
*Assistant Examiner*—Monique T. Cole
(74) *Attorney, Agent, or Firm*—McDonald Hopkins Co., LPA

(57) ABSTRACT

Urine samples are made free of potentially interfering substances, such as alkaloids or pharmaceuticals, by contacting the urine sample with an amount of a chemical oxidizing agent in a disposable oxidation bag, while retaining the physical indicia characteristic of urine to allow the sample to be further tested.

8 Claims, 3 Drawing Sheets

U.S. PATENT DOCUMENTS

| | | | |
|---|---|---|---|
| 4,661,100 A * | 4/1987 | Rechsteiner | 604/327 |
| 4,710,532 A * | 12/1987 | Hull et al. | 524/310 |
| 4,828,743 A | 5/1989 | Rhafield et al. | 252/87 |
| 4,877,744 A | 10/1989 | Chang | 436/162 |
| 4,955,879 A * | 9/1990 | Mervine | 604/327 |
| 4,979,402 A | 12/1990 | Ryan et al. | 73/863 |
| 5,036,014 A | 7/1991 | ElSohly et al. | 436/8 |
| 5,212,097 A | 5/1993 | Kamahori et al. | 436/111 |
| 5,350,855 A | 9/1994 | Daniloff et al. | 546/291 |
| 5,380,649 A | 1/1995 | Berry et al. | 435/22 |
| 5,384,246 A | 1/1995 | Berry et al. | 435/22 |
| 5,384,247 A | 1/1995 | Berry et al. | 435/22 |
| 5,403,749 A | 4/1995 | Khartchenko et al. | 436/132 |
| 5,409,814 A | 4/1995 | Berry et al. | 435/22 |
| 5,413,911 A | 5/1995 | Adamczyk et al. | 435/7.1 |
| 5,436,133 A | 7/1995 | Fujita et al. | 435/26 |
| 5,464,775 A | 11/1995 | Smith | 436/63 |
| 5,494,527 A | 2/1996 | Ludwig et al. | 134/3 |
| 5,501,958 A | 3/1996 | Berry et al. | 435/18 |
| 5,516,700 A | 5/1996 | Smith et al. | 436/164 |
| 5,759,860 A | 6/1998 | Smith et al. | 436/110 |
| 5,861,269 A | 1/1999 | Visor et al. | 435/26 |
| 5,925,570 A | 7/1999 | Nishidate et al. | 436/74 |
| 5,955,370 A | 9/1999 | Kell | 436/2 |
| 5,961,501 A * | 10/1999 | Cassidy et al. | 604/327 |
| 6,054,303 A | 4/2000 | Davalian et al. | 435/188 |
| 6,068,971 A | 5/2000 | Berry et al. | 435/4 |
| 6,162,647 A | 12/2000 | Stephens | 436/175 |
| 6,190,873 B1 | 2/2001 | Davalian et al. | 435/7.93 |
| 6,491,673 B1 * | 12/2002 | Palumbo et al. | 604/317 |

OTHER PUBLICATIONS

F. Urry, et al. "Nitrite Adulteration of Workplace Urine Drug–Testing Specimens 1. Sources and Associated Concentrations of Nitrite in Urine and Distinction Between Natural Sources and Adulteration", *Jr. of Anal. Toxicology*, vol. 22, pp. 89–95, 1998 (no month).

"Guidance for Reporting Specimen Validity Test Results", *NCLP Program Document #35*, Dept. of Health and Human Services, [Internet] http://workplac.samhsa.gov/ResourceCenter/DT/NLCP/PD35.html, pp. 1–4, Sep. 28, 1998.

E. King, "Performance of AdultaCheck 4 Test Strips for the Detection of Adulteration at the Point of Collection of Urine Specimens used for Drugs–of–Abuse Testing", Letter, *Jr. of Anal. Toxicology*, vol. 23, p. 72, Jan.–Feb. 1999.

A. Wu et al., Adulteration of Urine by "Urine Luck", *Clin. Chem.*, vol. 45, No. 7, pp. 1051–1057, 1999 (no month).

M. Blunt, Secretary of State, Missouri, "Rules of Department of Health, Division 25–Division of Administration, Chapter 30–Determination of Blood Alcohol by Blood, Breaths, Saliva and Urine Analysis, and Determination for the Presence of Drugs in Blood and Urine", Code of State Regulations, (19 CSR 25–30.070), p. 13, Nov. 1988.

M. Blunt, Secretary of State, Missouri, "Rules of Department of Health, Division 25–Division of Administration, Chapter 30–Determination of Blood Alcohol by Blood, Breath, Saliva and Urine Analysis; and Determination for the Presence of Drugs in Blood and Urine", Code of State Regulations, (19 CSR 25–30.011, 30.021, 30.031, 30.041, 30.050, 30.051,30.060,30.070, 3.080), pp. 1–27, Sep. 30, 2001.

* cited by examiner

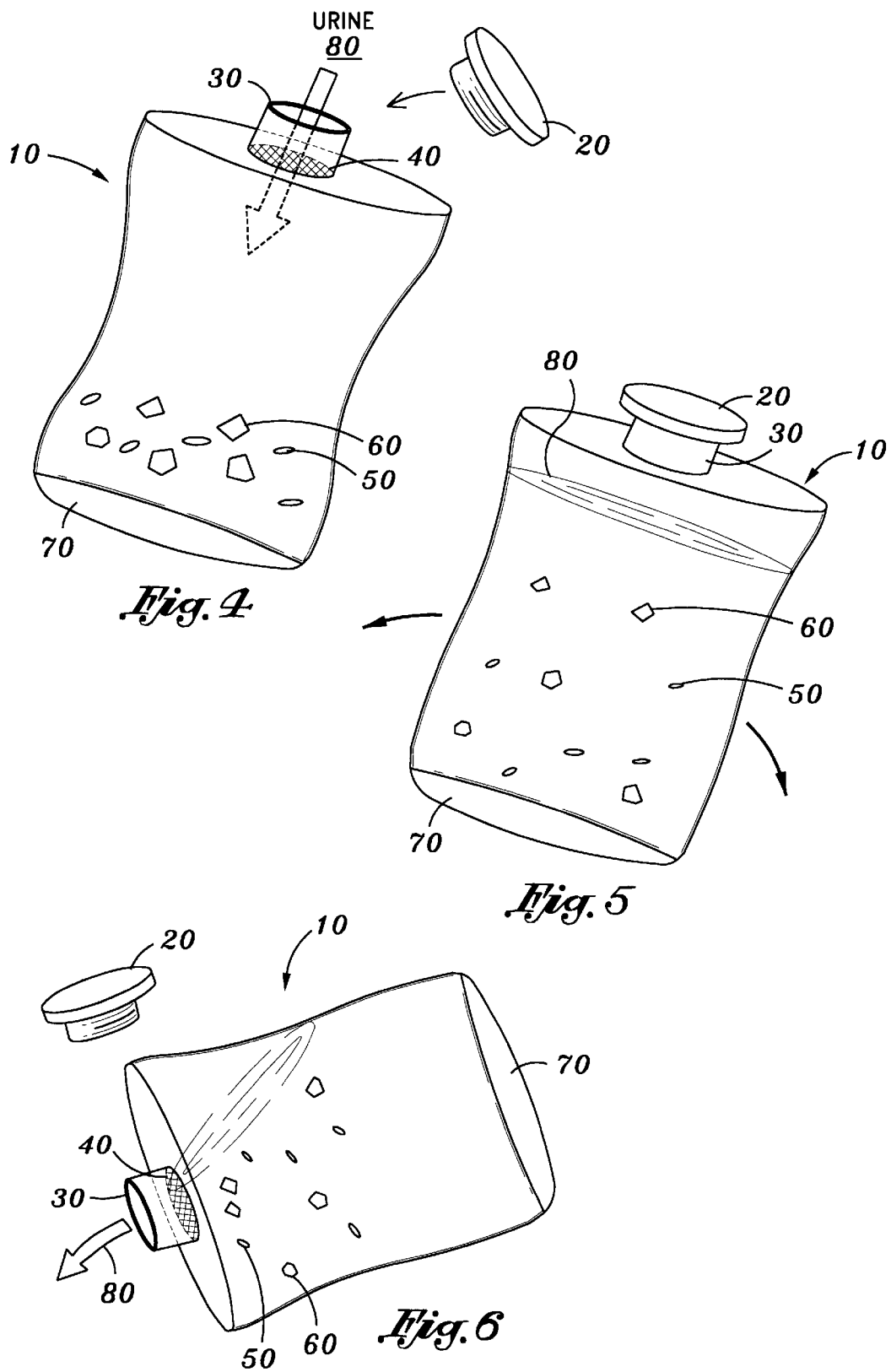

APPARATUS AND METHOD FOR REMOVING INTERFERING SUBSTANCES FROM A URINE SAMPLE USING A CHEMICAL OXIDANT

BACKGROUND OF THE INVENTION

1. Field of the Invention

The present invention generally relates to an apparatus and method of making urinalysis more accurate and, more specifically, this invention relates an apparatus and method to remove interfering substances from urine.

2. State of the Art

The kidneys remove unwanted substances circulating in the blood producing urine, which is excreted from the body. Consequently, diverse waste substances and other substances unwanted by the body find their way into urine for subsequent removal from the body. Urinalysis is the testing of the composition and amounts of waste substances in urine, and provides a tremendously powerful diagnostic tool for the medical profession. However, some of these unwanted substances can hide existing medical conditions, and some others can masquerade as non-existent medical conditions, undermining the usefulness of urinalysis as a medical diagnostic tool. Some unwanted substances that find their way into a urine sample are drugs and drug metabolites, given either as medicaments for conditions such as control of pain or nausea caused by chemotherapy, or voluntarily abused by the urine donor.

Recently, various immunoassays and other kinds of tests have been developed turning urinalysis into a powerful diagnostic tool. For example, quantities of drugs of abuse and other indicia of disease or bodily state can easily be detected by urinalysis. Some pharmaceuticals or other chemicals that might have been ingested disturb the sensitive tests making the actual state of the body difficult or impossible to determine. Among the substances that can be detected in urine, and used to diagnose medical conditions in the patient giving sample, are insulin, para-aminohippuric acid, phenol sulfonphthalein, phosphate, arylsulfatase-A, lysosome, urine amylase, total urine estrogens, specific estrogens, progestins, aldosterone, catecholamines, 5-hydroxyindol acetic acid, cortisol, homovanillic acid, human chorionic gonadotrophin, creatine, urea, uric acid, bilirubin, hemoglobin, hydroxyproline, melanin, porphorins, total protein, acid mucopolysaccharide, copper, glucose oxidase, and urine ketone. Removal of the potential masking components of urine can help make the various immunoassays or assays by other techniques, such as isolation followed by gas or liquid chromatography followed by mass spectrometry, more accurate.

One compound that may be found in urine results from the chemotherapy to relieve the distressing symptoms of cancer chemotherapy or voluntary ingestion from abuse is tetrahydrocannabinol. A method for detecting tetrahydrocannabinol is described in U.S. Pat. No. 5,036,013, issued to Sohly et al. In this patent, various deuterated cannabinoids were synthesized to help determine the quantitative amount of tetrahydrocannabinol in a urine sample. Various methods are described therein. But one method, in particular, involves spiking a urine sample with deuterated tetrahydrocannabinol and analyzing the resultant sample with gas chromatography/mass spectrum.

Another example of the problems created by interfering chemicals in urine is exemplified by the case of ibuprophen. Ibuprophen is a prostaglandin synthetase inhibitor that may be taken in large doses to relieve pain and inflammation characteristic of arthritis. When a patient taking these massive doses is subjected to urinalysis, it may mask other drugs of abuse, or may be mistaken for tetrahydrocannabinol. Such a misidentification of a drug of abuse can have devastating personal consequences for the tested patient.

However, the apparatus and methods of the prior art for detecting unwanted substances in urine are slow and costly. A urine sample is typically collected in a collection vessel and the vessel is then sent to a lab. Once in the lab, the urine sample must sometimes be transferred from the collection vessel to another apparatus, such as a test tube. Once the urine sample is in the test tube, chemicals are often added to the test tube to provide a colorometric indication of the presence of an unwanted substance. Such a procedure can result in delayed analysis and, consequently, delayed treatment of the patient.

A need therefore exists to overcome the disadvantages of the prior art.

SUMMARY OF THE INVENTION

In this present invention, an interfering substance such as tetrahydrocannabinol is removed from a urine sample by contacting the urine sample with a chemical oxidizing agent within an oxidative bag assembly. Therefore, removal of the interfering substance before a test improves the reliability of the test, and makes the test procedure quick and at a minimal cost.

In accordance with one aspect of the present invention, a disposable oxidative bag assembly comprises a bag body of flexible material made of either ethylene or polypropylene. The oxidative bag has closed sidewalls, a closed bottom end, a partial open top end, and a hollow interior. The oxidative bag assembly further includes an opening at the partial open top end to accept a tight sealing device to seal the oxidative bag assembly.

The disposable oxidative bag assembly in accordance with the present invention also comprises a chemical oxidant such as sodium persulfate ($Na_2S_8O_5$) or iodine pentoxide ($I_2O_5$) or N-bromosuccinimide ($NBrC_4H_4O_2$), activated carbon particles, and a silicon pillow within the hollow interior of the oxidative bag assembly. A mesch filter device within the partial open top prevents the escape of the activated carbon particles.

In accordance with another aspect of the present invention, a method to make urine samples free of potentially interfering substances, such as tetrahydrocannabinol, includes contacting the urine sample with a solution containing an amount of a chemical oxidizing agent in a disposable bag assembly. The amount of oxidizing agent is sufficient to oxidize between about 20 to 50% of the unwanted substance. The urine sample still retains physical indicia characteristic of urine allowing the sample to be further tested.

In another aspect of this invention, a urine sample is collected, then before any testing, an unwanted substance is removed from urine samples by contacting the urine sample in a disposable bag assembly with an amount of a chemical oxidizing agent and at least one hydrolysing acid sufficient to oxidize at least about 20% of the unwanted substance in a volume of urine while leaving the various physical indicia characteristic of urine unaffected, wherein the hydrolysing acid is a mineral acid selected from the group consisting of hydrochloric acid, n-hydroiodic acid, hydrobromic acid, and hydrofluoric acid.

In another aspect of this invention, a urine is collected, then before any testing, tetrahydrocannabinol is removed from the urine sample by contacting the urine sample with an amount of a chemical oxidizing agent consisting of sodium persulfate sufficient to oxidize at least about 20% of the tetrahydrocannabinol in a volume of urine while leaving the various physical indicia characteristic of urine unaffected.

These and other features, aspects and advantages of the present invention will become better understood with reference to the following drawings, descriptions and claims.

BRIEF DISCRIPTION OF THE DRAWINGS

FIG. 4 is a perspective view of the oxidation bag shown in FIG. 2 and showing a urine sample entering the bag.

FIG. 5 is a perspective view of the oxidation bag shown in FIG. 1 containing a urine sample.

FIG. 6 is a perspective view of the oxidation bag shown in FIG. 2 and showing a urine sample exiting the bag following oxidation.

DETAILED DISCRIPTION OF THE INVENTION

Figure 1:
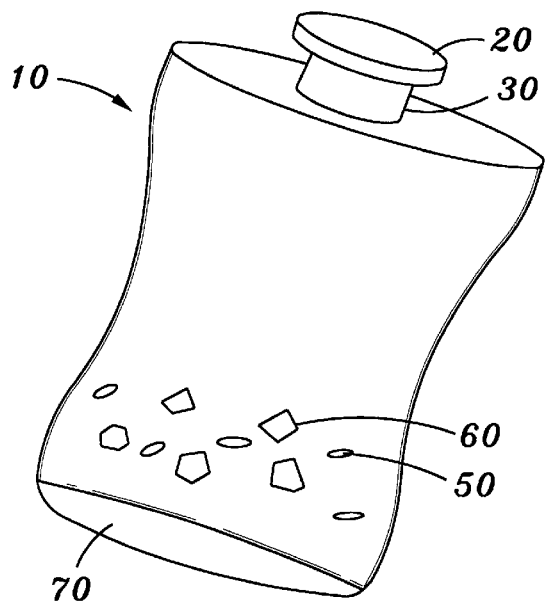
FIG. 1 is a perspective view of an oxidation bag with the tight sealing device attached, with sodium persulfate or iodine pentoxide or N-bromosuccinimide, carbon particles and a silicon pillow in accordance with the present invention.

In referring to FIG. 1, the apparatus of the present invention for oxidizing an unwanted substance, such as tetrahydrocannabinol, in a urine sample 80 comprises a disposable oxidation bag 10 that can be of various sizes. For example, the oxidation bag may usefully be about 3–5 ounces in size. While various materials may be used to form the oxidation bag 10, the material is preferably flexible and liquid impermeable, such as ethylene or polypropylene. The oxidation bag 10 may include closed sidewalls 11, a closed bottom end 12, a partial open top end 13, and a hollow interior 14 therein. A tight sealing device 20 attached (such as by threading) to a partial open top end 30 of the oxidative bag 10 creates a liquid tight seal. The size of the bag 10 may vary but is usefully about 4.5 inches high and about 3 inches wide. Inside the hollow interior 14 of the oxidative bag 10 is a chemical oxidizing agent 50, activated carbon particles 60, and a silicon pillow 70.

The particular oxidizing agent 50 may vary and include any agent known to oxidize organic components. Preferred agents include hydrogen peroxide, benzoyl peroxide, chromium trioxide, sodium permanganate, sodium persulfate, iodine pentoxide, N-bromosuccinimide, and potassium permanganate. Sodium persulfate and iodine are preferred because they do not leave trace elements in the urine sample. The oxidizing salts are preferably prepared as saturated solutions in deionized water, although more dilute solutions can be used. The aqueous solution of oxidizing agent is then added to the oxidation bag 10. It is preferred to use non-colored agents, as the urine may be subjected to various calorimetric tests.

Depending upon the size of the oxidation bag 10 and the amount of the urine sample 80, the amount of oxidizing agent 50 can vary. However, the amount of oxidizing agent is preferably sufficient to oxidize at least about 20%, preferably at least about 30%, and more preferably at least about 50% of the unwanted substance in a volume of urine 80. The chemical oxidizing agent 50 leaves the various physical indicia characteristic of urine substantially unaffected, and the trace substances that are not to be tested are removed.

The amount of activated carbon particles 60 is in an amount sufficient to reduce the oxidizing agent, such as sodium persulfate to sodium and sulfate which are normal constituents of urine 80, thereby leaving the various physical indicia characteristic of urine 80 unaffected. The silicon pillow 70 may have a configuration that allows it to be suitably placed within the configuration of the oxidation bag 10 and absorbs moisture that may be present in the oxidation bag 10 prior to a urine sample being placed therein.

Figure 2:
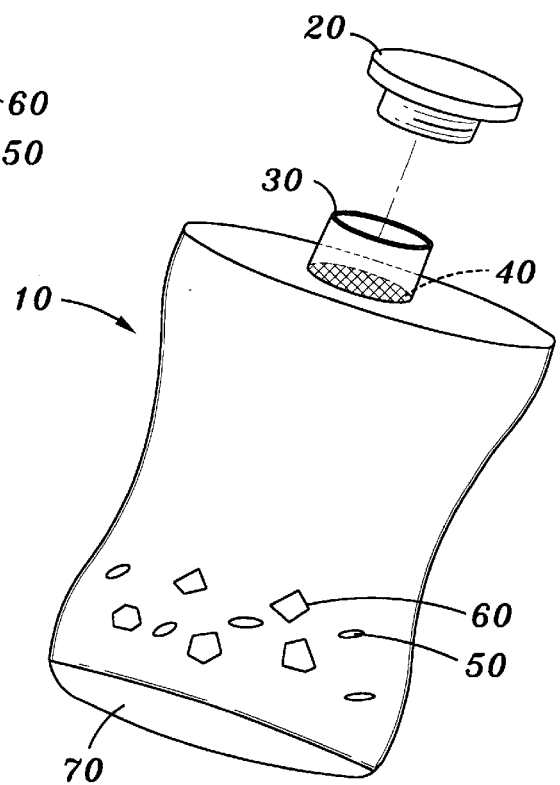
FIG. 2 is a perspective view of the oxidation bag shown in FIG. 1 but without the tight sealing device.
Figure 3:
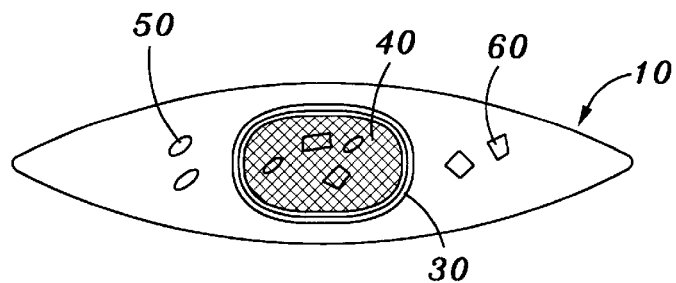
FIG. 3 is a top view of the oxidation bag shown in FIG. 2 and showing a mesch filter.

Now referring to FIGS. 2 and 3, the oxidative bag 10 may further include a mesch filter 40 enclosed in the partial open top end 30. The mesch filter 40 may have a pore size sufficient to prevent the carbon particles 60 from exiting the open top end 30 when the tight sealing device 20 is not attached to the open top end 30. Thus, the mesch filter 40 may have a pore size between about 50 to 300 μm.

In FIGS. 4 and 5, it can be seen that a subject may void a urine sample 80 directly into the oxidation bag 10. Upon doing so, the sealing device 20 may be attached to the open top end 30. The urine sample 80 may then mix with the oxidizing agent 50 and the carbon particles 60. From such mixing, the oxidizing agent 50 oxidizes the unwanted substance such that the urine sample 80 may then be emptied from the bag 10 (FIG. 6) and subjected to desired analysis.

Figure 7:
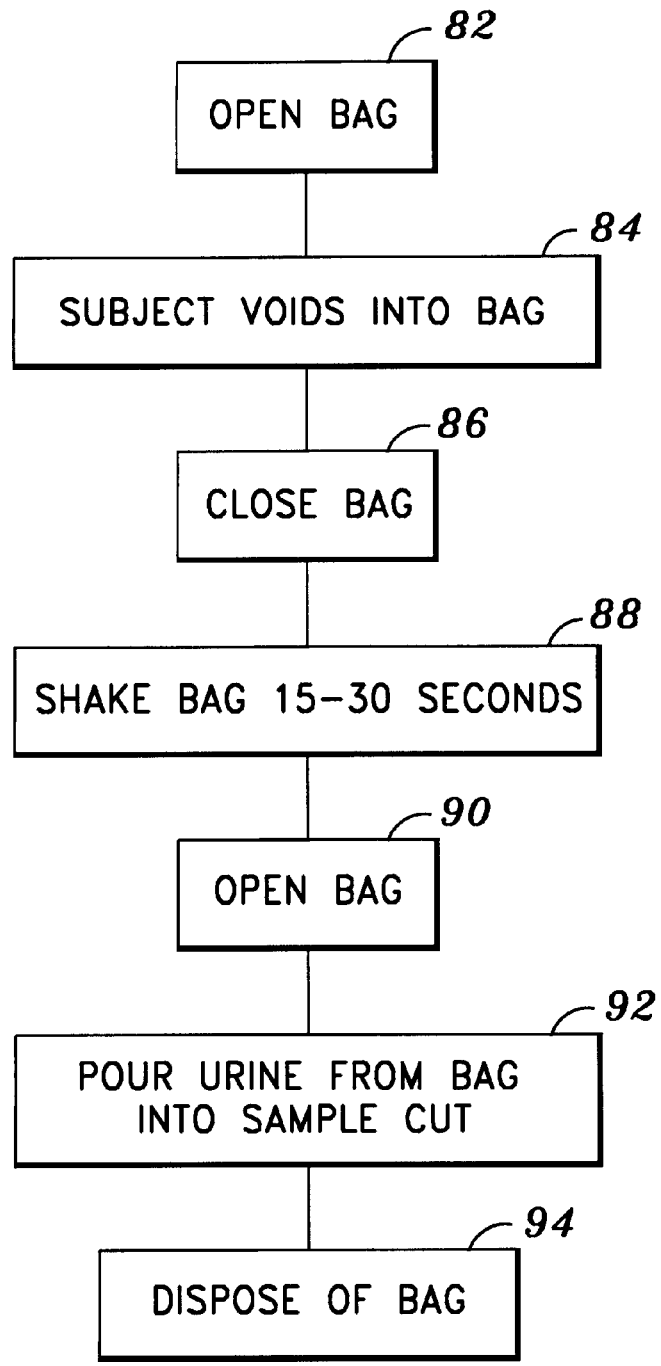
FIG. 7 is a flow chart depicting the steps of the present invention.

FIG. 7 further depicts a method of the present invention. Therein, a step 82 includes opening the oxidation bag 10, and in step 84, a subject voids directly into the bag 10. In step 86, the bag 10 is closed and then shaken for a period of time in step 88 sufficient to oxidize at least about 20% of the unwanted substance. In step 90, the bag 10 is opened so that the urine sample 80 can be emptied into another vessel in step 92. Finally, the bag 10 may be discarded in step 94.

In another preferred embodiment, a hydrolysing acid may be included as an ingredient of the oxidizing agent 50. The hydrolysing acid of the invention is preferably a mineral acid or an organic acid. Preferred mineral acids include, but are not limited to, hydrochloric acid, nitric acid, sulfuric acid, sodium bisulfate acid, phosphoric acid, polyphosphoric acid, monosodium phosphate acid, disodium phosphate acid, perchloric acid, hydroiodic acid, hydrobromic acid, and hydrofluoric acid. Organic acids may be selected from those acids having the general formula of R—(COOX)y where R is any lower alkyl or aryl radical having 1 to 6 carbon atoms, x may be the same or different an may be hydrogen or alkali or alkaline earth metals, provided that at least one X is a hydrogen, and y is a number between 1 and 3. Preferred alkali and alkaline earth metals include lithium, sodium, potassium, berylium, calcium, and magnesium. X may be chosen from the group including zinc and manganese as well. Preferred organic acids include, but are not limited to, acetic acid, formic acid, oxalic acid, mono-sodium oxalic acid, propionic acid, malic acid, mono-potassium malic acid, butyric acid, succinic acid, citric acid, tartaric acid, benzoic acid, pthalic acid, mono-potassium pthalic acid, and flouroactic acid. Organic acids having four or fewer carbon atoms having one, two or three carboxyl groups are especially preferred for this invention. Although it is not necessary, it is preferred that the.acid be monoprotic, that is, that it have only ndone acidic hydrogen atom.

In general, any water-soluble acid would be useful, but for purposes of this invention, it is preferred that the anion left by the acid be an anion normally found in urine. Therefore, the more preferred mineral acid for use in this invention is hydrochloric acid and the preferred organic acids are tannic acid, citric acid, and acetic acid. The concentration of the hydrolysing acid to be added to the urine sample has a concentration greater than 1 Normal, more preferably greater than 3 Normal, and most preferably greater than 3.5 Normal. The pH of the hydrolysing acid solution is preferably between about 1 and 0.75.

The hydrolysing acid solution used in this invention can be a mixture of a primary, or first acid and a secondary, or second acid. The first acid can be one of the acids listed above and the second acid can be one acid or a combination of more than one acid in a solution. For example, the second acid may be one or more acids selected from the group of hydrochloric acid, nitric acid, sulfuric acid, sodium bisulfate, sodium persulfate, phosphoric acid, monosodium phosphorate, disodium phosphorate, perchloric acid, hydroiodic acid, or an organic acid selected from the group of organic acids having the general formula of R—(COOX)y where R is any lower alkyl or aryl radical having 1 to 6 carbon atoms, X may be the same or different and is hydrogen or alkali or alkaline earth metals, provided that at least one X is hydrogen, and y is any number between 1 and 3. Preferred alkali and alkaline earth metals include lithium, sodium, potassium, berllium, calcium and magnesium. Preferred organic acids include acetic, formic, oxalic, monosodium oxalic, propionic, malic, monopotassium malic acid, butyric, succinic, citric, tartaric, benzoic, pthalic, potassium hydrophthalic acid, and flouroacetic acids. Organic acids having four or fewer carbon atoms having one or two carboxyl groups are preferred for this invention. The concentration of the acidic hydrogen in any combination of acids to be added to the urine sample has an effective concentration of greater than 1 Normal, more preferably greater than 3 Normal, and most preferably greater than 3.5 Normal. Effective concentration means that a solution of a combination of acids is 1N if 1 liter of 1N sodium hydroxide solution exactly neutralizes 1 liter of the acid combination. The solution exactly neutralizes 1 liter of the acid combination. The pH of the combination acid solution will be between about 2 and 0.5, preferably between 1 and 0.75.

One particularly preferred acid for use in this invention is 20 Baum, hydrochloric acid that has been cut to between 10 and 30 volume percent, more preferably, between about 15 and 25 volume percent, by water.

Preferably, the acid added to a urine sample does not harm other indicia present in urine. Such indicia are used for diagnosis of disease, and bodily state, such as pregnancy. Such indicia include, pH, saccharide content, red blood cell count, nitrogen content, albumin content, protein content, immunoassayable proteins, and total solids content. Immunoassayable proteins include HCG, and other proteins used to diagnose congenital diseases, cancer, and other abnormalities. It is preferred that the method of the invention leaves the indicia required for successful testing of insulin levels, paraaminohuppuric acid, phenol sulfonphthalein, phosphate, arylsulfatase-A, lysosome, urine amylase, total urine estrogens, specific estrogens, progestins, aldosterone, catecholamines, 5-hydroxyindoleacetic acid, cortisol, homovanillic acid, human chorionic gonatrophin, creatine, urea, uric acid, bilirubin, hemoglobin, hydroxyproline, melanin, porphorins, total protein, acid mucopolysaccharide, copper, glucose oxidase, and urine ketone substantially unaffected.

Preferably, adding the hydrolysing solution of this invention removes at least about 25% of the interfering substances, preferably at least about 33%, and most preferably at least about 50%, when measured on a wt/volume basis.

In general, the unwanted substances removed by this invention are natural products or pharmaceuticals. Preferably the substances are alkaloids or other naturally occurring substances. In another embodiment, the unwanted substances are selected from the group consisting of testosterone, estrogen, progesterone, anabolic steroids, ibuprophan, acetaminophen, acetosalicylic acid, benzedrine, 3,4,5-trimethoxy-benedrine, tetrahydrocannabinol, cocaine, morphine, codeine, nicotine, ethyl alcohol, and acetaldehyde.

In another preferred embodiment of this invention, an unwanted substance, tetrahydrocannabinol, is removed from the urine sample through oxidation with a chemical oxidizing agent such as sodium persulfate. The urine sample is contacted with the sodium persulfate in an amount sufficient to oxidize at least about 20% of the tetrahydrocannabinol in a volume of urine. Additionally, the method of this invention can remove a substantial amount of the unwanted substances while not interfering with the other indicia for the various tests enumerated above.

EXAMPLES

The invention can be better understood by reference to the following illustrative examples of the preferred embodiment of the invention, which examples are meant to illustrate the invention and not to limit the scope of the invention in any way.

Example 1

In this example, a urine additive solution is made.

30 mls of commercially obtained aqueous 50% hydrogen peroxide is added to enough deionized water to make 100 mls of solution. This solution is used in the following Examples.

Similarly, a chemical oxidizing agent solution can be made with aqueous peroxide, saturated aqueous chromium trioxide, saturated aqueous sodium permanganate, and saturated aqueous potassium permanganate solutions.

Example 2

In this example, various additives are added to the solution of Example 1 to create solutions that can remove interfering solutions.

10 mls of commercially obtained 20 Baum, chromic acid is added to 100 mls of the solution of Example 1 making an oxidizing-hydrolysing solution.

Similarly, new oxidizing-hydrolysing solutions are made adding acetic, nitric, sulfuric, sodium bisulfate, phosphoric, monosodium phosphorate, disodium phosphorate, perchloric, hydroiodic, hydrobromic, hydrofluoric acetic, formic, oxalic, sodium hydrooxalic acid, proprionic, malic, potassium hydromalic acid, butyric, succinic, citric, tartaric, benzoic, phthalic, potassium hydrophtalic acid, and flouroacetic acids to the solution of Example 1.

Example 3

In this example, various additives are placed in the solution of example 2.

In another preferred embodiment, 10 ml of potassium hydrophthalic acid is added to the solution of Example 2, producing an oxidizing-diacidic. hydrolysing solution useful for the process of this invention.

Similarly, new solutions are made adding nitric, sulfuric, sodium bisulfate, phosphoric, monosodium phosphorate, disodium phosphorate, perchloric, hydroiodic, hydrobromic, hydrofluoric acetic, formic, oxalic, sodium hydrooxalic acid, propionic, malic, potassium hydromalic acid, butyric, succinic, citric, tartaric, benzoic, phthalic, and flouroacetic acids to the solution of Example 2.

Example 4

In this example, the solution of Example 1 is used to remove unwanted interfering substances from a urine sample. Urine samples are collected in conventional ways. The samples are divided into two equal aliquots. The control is analyzed in the usual way without any further preparation. 10 mls of the oxidizing-hydrolysing solution of Example 2 are added to the second aliquot. The samples are worked up by first separating the sample using gas chromatography, and subsequent analysis by mass spectroscopy. Typically expected results, tabulated by aliquot are presented in Table 1.

TABLE 1

| ALIQUOT # | THC ng/Ml | % REDUCTION | pH | SPECIFIC GRAVITY |
|---|---|---|---|---|
| 1a | 1225 |  | 5 | 1.03 |
| 1b | 735 | 40% | 5 | 1.03 |
| 2a | 75 |  | 5 | 1.01 |
| 2b | 48 | 35% | 5 | 1.01 |
| 3a | 50 |  | 6 | 1.01 |
| 3b | 35 | 30% | 6 | 1.01 | where "a" and "b" in the aliquot number refer to the two aliquots produced from the same original sample sent to the testing laboratory.

Table 1 indicates that the oxidizing-hydrolysing solution may reduce the presence of tetrahydrocannabinol by an average of 35% regardless of the initial concentration of the amount of interfering substances. The pH of the samples, one of the normal indicia tested in standard urinalysis, remains substantially unchanged after the use of the oxidizing-hydrolysing solution, as does the specific gravity.

Similar results are observed when the hydrolysing acid from Examples 1 and 3 are substituted for the oxidizing-hydrolysing solution of Example 2 in the test protocol outlined above.

Example 5

The procedure of Example 4 was used except that sodium persulfate, iodine pentoxide, and N-bromosuccinimide were used as the oxidizing agent. The following Tables indicate the results:

TABLE 2 sodium persulfate

| | (all weight in grams) | | | Results | Blank | % THCA |
|---|---|---|---|---|---|---|
| # | Na2O8 | Carbon | Urine | Test | (ng/ml) | (ng/ml) | Reduction |
| 1 | 0.10 | 1.00 | 69.55 | FPIA | 58.6 | 221 | 73.5% |
| 2 | 0.15 | 1.00 | 61.07 | FPIA | 54.7 | 221 | 75.2% |
| 3 | 0.27 | 1.01 | 60.03 | FPIA | 52.7 | 221 | 76.2% |
| 4 | 0.25 | 0.98 | 60.08 | FPIA | 52.7 | 221 | 76.2% |

TABLE 3 iodine pentoxide

| # | ng/ml Sample | ng/ml Results | Blank | Reduct. | pH | Test |
|---|---|---|---|---|---|---|
| 1 | 734 | 0 | 393 | 100% | xxx | emit ria |
| 2 | 733 | 0 | none | xxx | 5.0 | Emit/GC/MS |
| 3 | 801 | 0 | 525 | 100% | xxx | emit/ria |
| 4 | 810 | 0 | 525 | 100% | xxx | emit/ria |
| 5 | 814 | 0 | 525 | 100% | xxx | emit/ria |
| 6 | 818 | 0 | 525 | 100% | xxx | emit/ria |
| 7 | 819 | 0 | none | none | xxx | Emit/GC/MS |
| 8 | 824 | 0 | 546 | 100% | 5.0 | FPIA |
| 9 | 825 | 0 | 546 | 100% | 5.0 | FPIA |
| 10 | 826 | 0 | 546 | 100% | 5.0 | FPIA |
| 11 | 827 | 0 | 546 | 100% | 5.0 | FPIA |
| 12 | 831 | 0 | none | none | 5.0 | Emit/GC/MS |

| Test | Cutoff ng/ml |
|---|---|
| emit | 50 |
| fpia | 50 |
| ria | 50 |
| gc/ms | 15 |

TABLE 3

N-bromosuccinimide

| # | ng/ml Sample | ng/ml Results | Blank | Reduct. | pH | Test |
|---|---|---|---|---|---|---|
| 1 | 1107 | 0 | 509 | 100% | — | emit/ria |
| 2 | 1118 | 0 | — | — | — | emit/gcms |
| 3 | 1119 | 21 | — | — | — | emit/gcms |
| 4 | 1120 | 54 | — | — | — | emit/gcms |
| 5 | 1202 | 0 | 341 | 100% | — | emit/ria |
| 6 | 1203 | 146 | — | — | — | emit/ria |
| 7 | 1209 | 0 | — | — | — | emit/gcms |
| 8 | 1210 | 71 | — | — | — | emit/gcms |
| 9 | 1211 | >200 | — | — | — | emit/gcms |
| 10 | 1212 | >200 | — | —% | — | emit/gcms |

It should be understood, of course, that the forgoing descriptions and examples relates to preferred embodiments of the invention, and that modifications may be made without departing from the spirit and scope of the invention as set forth in the following claims.

We claim:

1. A apparatus to remove an unwanted substance from urine, comprising:

a disposable oxidation bag having closed side walls, a closed bottom end, a partial open top end, and a hollow interior therein;

an oxidative agent in the hollow interior;

carbon particles in the hollow interior;

a mesh filter adjacent the partial open top end; and a sealing device that can be placed over the partial open top end.

2. The apparatus of claim 1, wherein the oxidation bag comprises a flexible, liquid impermeable material.

3. The apparatus of claim 2, wherein the flexible material comprises one of polypropylene and ethylene.

4. The apparatus of claim 1, wherein the oxidizing agent is present in an amount sufficient to oxidize at least about 20% of the unwanted substance.

5. The apparatus of claim 1, wherein the oxidizing agent comprises sodium persulfate.

6. The apparatus of claim 1, wherein the oxidizing agent comprises iodine pentoxide.

7. The apparatus of claim 1, wherein the oxidizing agent comprises N-bromosuccinimide.

8. The apparatus of claim 1, further comprising a silicon pillow within the hollow interior.

* * * * *